United States Patent
Tobe

(10) Patent No.: US 7,300,674 B2
(45) Date of Patent: Nov. 27, 2007

(54) STERILE LOW BICARBONATE DIALYSIS CONCENTRATE SOLUTIONS

(76) Inventor: Sheldon Tobe, A240-2075 Bayview Avenue, Toronto, Ontario (CA) M4N 3M5

( * ) Notice: Subject to any disclaimer, the term of this patent is extended or adjusted under 35 U.S.C. 154(b) by 440 days.

(21) Appl. No.: 10/020,882

(22) Filed: Dec. 19, 2001

(65) Prior Publication Data

US 2002/0077580 A1    Jun. 20, 2002

Related U.S. Application Data

(60) Provisional application No. 60/256,493, filed on Dec. 20, 2000.

(51) Int. Cl.
*A61K 33/10* (2006.01)
*A61K 33/14* (2006.01)
*A61K 31/194* (2006.01)
*A61P 7/08* (2006.01)

(52) U.S. Cl. .................. 424/680; 424/681; 424/717; 514/574

(58) Field of Classification Search ............... 424/680, 424/681, 717
See application file for complete search history.

(56) References Cited

U.S. PATENT DOCUMENTS

| | | | |
|---|---|---|---|
| 4,630,727 A | 12/1986 | Feriani et al. | 206/221 |
| 5,211,643 A | 5/1993 | Reinhardt et al. | 604/416 |
| 5,945,449 A | 8/1999 | Purcell et al. | 514/512 |
| 6,492,336 B1 * | 12/2002 | Mahiout | 514/25 |

FOREIGN PATENT DOCUMENTS

| | | |
|---|---|---|
| DE | 41 14 908 A1 | 11/1992 |
| WO | WO 96/01118 | 1/1996 |

OTHER PUBLICATIONS

Chemical Abstracts 124:325351 (1996).*
Koo, S.K. et al., "Calcium-free hemodialysis for the management of hypercalcemia," Nephron, vol. 72, pp. 424-428 (1996).*
Yatzidis et al., "Hemodialysis with a New Single Stable Bicarbonate Dialysate", Nephron, vol. 64, 1993; 27-31.
F. H. Leenen, et al., "Hemodynamic Changes During Acetate and Bicarbonate Hemodialysis", Artificial Organs 8(4), 1984; 411-417.
M. Kaye et al., "Calcium-free Dialyzate: Development and Applications", Clinical Nephrology, vol. 31, No. 3, 1989; 132-138.
M. Kaye and D. Fisher, "Changes in Intact Parathyroid Hormone Levels During Hemodialysis Following Exposure to Either Differing Dialyzate,Calcium Concentrations or Calcium-Free Dialysis with Varying Calcium Infusion Rates", Clinical Nephrology, vol. 34, No. 2, 1990; 84-87.
M. Kaye, "Long-term studies using a calcium-free dialysate", Clinical Nephrology, vol. 40, No. 4, 1993; 221-224.
P.Y.W. Tam et al., "Slow Continuous Hemodialysis for the Management of Complicated Acute Renal Failure in an Intensive Care Unit", Clinical Nephrology, vol. 30, No. 2, 1988; 79-85.
E.F.H. Van Bommel et al, "Acute Dialytic Support for the Critically Ill: Intermittent Hemodialysis Versus Continuous Arteriovenous Hemodiafiltration", Am. J. Nephrol., vol. 15, 1995; 192-200.
E.F.H. Van Bommel, "Are Continuous Therapies Superior to Intermittent Haemodialysis for Acute Renal Failure on the Intensive Care Unit", Nephrol Dial. Transplant 1995 Edit. Comm., p. 311.
A. Davenport et al., "Hyperlactataemia and Metabolic Acidosis During Haemofiltration Using Lactate-Buffered Fluids", Nephron, vol. 59, 1991; 461-465.
M. Leblanc et al., "Bicarbonate Dialysate for Continuous Renal Replacement Therapy in Intensive Care Unit Patients With Acute Renal Failure", Am. J. Kidney Diseases, vol. 26, No. 6, 1995; 910-917.
Knaus W.A. et al., "APACHE II: A Severity of Disease Classification System", Critical Care Med., vol. 13, No. 10, 1985; 818-827.
Jordan, D.A. et al., "Evaluation of Sepsis in a Critically ill Surgical Population", Critical Care Med., vol. 15, No. 10, 1987; 897-904.

* cited by examiner

Primary Examiner—John Pak

(57) ABSTRACT

The present invention relates to a sterile calcium-free low bicarbonate dialysis concentrate composition for use in conjunction with regional citrate anti-coagulation in the context of either dialysis or hemofiltration. Methods of use of the sterile calcium free low bicarbonate dialysis concentrate compositions are also disclosed. The low bicarbonate concentrate takes into account the fact that citrate is hepatically metabolized into bicarbonate, thus minimizing metabolic complications.

9 Claims, No Drawings

STERILE LOW BICARBONATE DIALYSIS CONCENTRATE SOLUTIONS

This application claims benefit of Provisional Application 60/256,493, filed on Dec. 20, 2000.

FIELD OF THE INVENTION

The present invention relates to a sterile concentrate dialysis solution. More particularly, it relates to a sterile calcium-free low bicarbonate concentrate solution for use in dialysis and hemofiltration.

BACKGROUND OF THE INVENTION

The purification of blood and separation of fluids using dialysis can be advantageously used in many medical applications, particularly conditions where renal function has significantly declined. Dialysis removes wastes from blood through a semipermeable membrane by diffusive or convective processes. There are two principal dialysis methods used to support patients requiring renal replacement therapy: hemodialysis and peritoneal dialysis.

Hemodialysis, involves the removal of solutes and fluids (such as urea, creatinine and uric acid) from the blood through a dialysis membrane by diffusion into a dialysate. The dialysis membrane is a semipermeable membrane which is typically made of cellulose. Blood solutes containing the waste permeate through the membrane and into a dialysis solution or dialysate formulated to control solute net movement through the membrane.

In the chronic hemodialysis setting, processes which have been developed and are commonly used provide bicarbonate dialysis using a highly sophisticated machine which can be monitored by a team. Dialysis provided in the intensive care setting for patients with an acute loss of kidney function has traditionally been provided with a chronic hemodialysis machine, brought into the unit and operated by one dialysis nurse per patient, in addition to the patient's intensive care nurse.

Hemodialysis can be either continuous or intermittent. Intermittent hemodialysis involves short intensive periods of treatment on alternate days, while continuous hemodialysis involves continuous fluid removal and continuous blood purification, often with a machine dedicated for this purpose.

Due to resource limitations dialysis often must be condensed into a period of hours and may be limited to less than daily treatments leading to large fluctuations in levels of the substances removed from the patient. These fluctuations may adversely affect patient outcomes. A dialysis therapy which comes closest to normal kidney function, by operating continuously may improve patient outcomes and shorten intensive care stays. This has led to the adoption of continuous modalities of renal replacement therapy (CRRT) in the intensive care setting.

Continuous renal replacement therapy (CRRT) is dialysis continued 24 hours a day. Unlike chronic hemodialysis there are no standardized equipment or processes for CRRT. To simplify the equipment necessary, CRRT does not use dialysate from concentrate, but uses pre-made dialysate, usually peritoneal dialysis solution. This solution is sterile and is buffered by lactate. The dialysis solution to which blood is exposed through this membrane should have the same electrolyte composition of normal serum or it may induce fatal electrolyte abnormalities. Its use with dialysis filters requires at a minimum the absence of pyrogens. If the solution is to be given intraperitoneally or intravenously it must be sterile and pyrogen free.

The electrolyte composition of all dialysis solutions may vary but in a narrow range. The major cationic electrolyte component is sodium, usually at the concentration it is found in serum 140 (mmol/L, mEq/L). Other cations include calcium (2.5 mmol/L, 5.0 mEq/L) and magnesium (0.75 mmol/L, 1.5 mEq/L). The major anion is chloride whose concentration is determined by the net of the cationic charge constituents less the anionic buffer. The dialysis solutions used in all forms of dialysis contain buffers in an attempt to correct metabolic acidosis. Common buffers used include bicarbonate, lactate and acetate buffers.

Bicarbonate buffer is a preferred buffer for dialysis since bicarbonate is the physiological buffer of the body. However, pre-made mixtures of bicarbonate buffered solutions are difficult to sterilize and store because released carbonate will precipitate with calcium if present. Attempts have been made to stabilize calcium, for example with glycylglycine (U.S. Pat. No. 5,211,643 to Reinhardt et al). Continuous dialysis against an agent such as glycylglycine produces levels in the blood close to those present in the dialysate. The effect of long term exposure to stabilizing agents such as glycylglycine is unknown (Yatzidis et al. Nephron., 64:27-31, 1993).

Furthermore, sugars in a dialysis solution will caramelize during heat sterilization and prolonged exposure if kept at neutral or higher pH (7.4). Therefore sugar containing dialysis solution is kept at low pH. For example, pH 5.4 for most peritoneal dialysis solutions. The low pH is believed to be the source of pain patients suffer after instillation of a fresh bag of peritoneal dialysis solution. Low pH solutions are known to reduce the effectiveness of peritoneal immunologic defences. The safety of using low pH solutions for dialysis or hemofiltration during CRRT has not been studied.

Also, during preparation and storage of a bicarbonate buffered solution, $CO_2$ is released from the solution, changing the bicarbonate concentration and pH of the solution. It is therefore necessary for bicarbonate containing solutions to be stored in glass or $CO_2$ impermeable plastic containers. The following solutions have been proposed to control the $CO_2$ content of the bicarbonate solution for peritoneal dialysis: storage in a powder form until use; use of an impermeable barrier between calcium containing and bicarbonate containing portions; and addition of buffers such as histidine or glycylglycine (H. Yatzidis, Nephron 64:27-31, 1993).

Dialysis care has become process driven to maximize the quality of the dialysis and to minimize costs. Hemodialysis machines have been developed which can prepare dialysis solution online from a single concentrate and clean water provided from a central reverse osmosis system. To get around the stability problems associated with calcium and bicarbonate, acetate was substituted for bicarbonate. Acetate hemodialysis was carried out until evidence showed the deleterious effects of acetate on dialysis patients, particularly with the use of the newer more biocompatible dialysis membranes (F. H. Leenen, Artificial Organs 8:411-417, November 1994).

Dual proportioning dialysis machines have been developed and employed at great expense to provide bicarbonate dialysis. These machines solve the calcium bicarbonate instability problem by keeping the bicarbonate and acid concentrates separate until the time of dialysis. Although micro precipitation may occur immediately after mixture, clinically this is not a concern even over a 72 hour period (Leblanc et al, 1995). However, because of this precipitation bicarbonate dialysis machines must have acid rinses on a regular basis.

Separate batches of concentrates have been used using split bags which contain calcium and magnesium on the one hand, and the bicarbonate on the other hand to prevent precipitation (U.S. Pat. No. 4,630,727 to Feriani et al).

A method was been developed to allow an older single proportioning chronic dialysis machine to produce bicarbonate dialysis from concentrate using calcium free bicarbonate concentrate adding the calcium back into the blood by an infusion pump. This method for chronic dialysis was reported by Kaye et al, but was not adopted outside of Kaye's unit in Montreal. (M. Kaye et al., Clinical Nephrology 31:132-138, 1989; M. Kaye and D. Fisher, Clinical Nephrology 34:84-87, 1990; and M. Kaye, Clinical Nephrology 40:221-224, 1993). Calcium is infused distal to the dialyzer into the drip chamber using an infusion pump and is a component of the dialysate. In Kaye's studies, the patient's are not critically ill and his system is set up for chronic hemodialysis, not for acute hemodialysis. The concentrate used by Kaye is not sterile. Furthermore, Kaye's system is used for intermittent, but not for continuous dialysis.

Acute renal failure in critically ill patients, which is generally accompanied by metabolic derangements and high overall mortality, poses significant challenges for renal replacement therapy. Acute intermittent hemodialysis has been the conventional therapy. Bicarbonate dialysate which is typically used in acute intermittent hemodialysis is not sterile but only clean.

Problems with the rapid removal of fluid and changes in electrolytes which occur during high efficiency short term intermittent hemodialysis have led to the development and use of continuous renal replacement therapies (CRRT) for critically ill patients (P. Y. W. Tam et al., Clinical Nephrology 30:7985, 1988 and E. F. H. Van Bommel et al, Am. J. Nephrol. 15:192-200, 1995). Solute and volume removal are slow and continuous during CRRT eliminating the large shifts occurring between body compartments during intermittent hemodialysis, which may lead to hypotension and interfere with renal recovery (E. F. H. Van Bommel, Nephrol. Dial. Transplant. 1995 Editorial Comments, p. 311). CRRT techniques include peritoneal dialysis, continuous arterio-venous and veno-venous ultrafiltration, hemofiltration, hemodialysis and hemodiafiltration. Traditionally CRRT has used peritoneal dialysis solution as the dialysate and infusate.

Lactate containing peritoneal dialysis solution has been used in CRRT dialysate with some success (Baxter and Gambro solutions). Lactate is stable with calcium and is stable at low pH (5.4). Lactate is metabolised by the intact functioning liver into bicarbonate, the body's natural buffer. However, lactate infusions are known to induce panic in susceptible individuals and may alter metabolism to favour catabolism over anabolism (R. L. Veech et al.). Its safety in CRRT dialysis has not been tested. However, its use as a buffer in peritoneal dialysis solution is universal and appears to be tolerated, except for abdominal pain and possible immunologic effects; there is mounting evidence that exposure to large amounts of lactate, particularly in the racemic form, may not be benign. Lactate included in these solutions is of the racemic form.

In intensive care patients, such as patients who have developed hypotension and lactic acidosis, lactate from the dialysis solution may not be metabolized to bicarbonate because of liver dysfunction, and when the dialysate lacks bicarbonate, acidosis may be worsened due to bicarbonate removal during dialysis. (A. Davenport et al., Nephron 1991:59:461-465, 1991 and M. Leblanc et al., Am. J. Kid. Dis. 26:910-917, 1995). For acute hemodialysis in the intensive care unit CRRT typically uses lactate based sterile solutions as dialysate and infusate (peritoneal dialysis solution). Research into methods to provide bicarbonate dialysate have been ongoing. Recently, a method was reported for providing non-sterile calcium bicarbonate dialysate for patients in the intensive care undergoing CRRT (M. Leblanc, AJKD 26(6):910-917, 1995). Non-sterile bicarbonate dialysis solutions can be produced in the chronic hemodialysis unit or hospital pharmacy and carried to the intensive care unit. These methods are labour intensive, unregulated, non sterile, not pyrogen free, expensive and may lack sufficient quality control. Unlike chronic hemo- or peritoneal dialysis, which are process driven and carried out in a uniform, cost effective quality controlled manner, CRRT is carried out in many different modalities specific to each intensive care unit.

It is important to use a sterile dialysis solution in CRRT in order to avoid pyrogenic reactions caused by bacteria and endotoxin contamination of the dialysate solution. It is also important to have a solution which is readily available for use. While sterile lactate or acetate based dialysis solutions may be used in CRRT they suffer from the disadvantages discussed above. It has been suggested that bicarbonate dialysate may be preferable to lactate or acetate-based solutions (M. Leblanc et al., Am. J. Kid. Dis. 26:910-917, 1995).

Furthermore, CRRT requires the addition of an anti-coagulent to the dialysate to prevent thrombosis. Standard techniques use systematic heparin as an anti-coagulent. However, many critically ill patients cannot tolerate heparin due to hemorrhage, severe coagulopathy, or heparin induced thrombocytopenia. For these reasons, citrate has been used as an effective regional anti-coagulant and is now accepted as the anticoagulent of choice for patients on CRRT. Citrate is an organic acid which is hepatically metabolized to bicarbonate. Research has shown that patients differ in their sensitivity to bicarbonate in the dialysate. For instance, in some patients excessive bicarbonate may result in alkalemia, whereas, in some patients insufficient bicarbonate may result in acidemia. Therefore, if citrate is used as the anti-coagulent, then it is crucial that the concentration of bicarbonate in the dialysate be low or absent, depending on the sensitivity of the individual patient. Since the prior art dialysate solutions did not take into account the bicarbonate derived from citrate, the total effective bicarbonate concentrations tended to be too high resulting in metabolic complications. To address the aforementioned problems, pharmacists have begun to produce bicarbonate-free dialysate solutions in the laboratory. However, as discussed above, these methods are labour intensive, unregulated, non sterile, not pyrogen free, expensive and may lack sufficient quality control.

Accordingly, there exists a need for a sterile calcium-free low bicarbonate concentrate for quickly and easily preparing dialysate solutions for use in dialysis and hemofiltration.

SUMMARY OF THE INVENTION

This invention generally relates to concentrates and corresponding diluted dialysis solutions with reduced bicarbonate concentrations and methods and uses therefor. CRRT requires the addition of an anti-coagulent such as citrate to either the dialysate or directly infused into the blood entering the extracorporeal circuit to prevent thrombosis. Citrate is an organic acid which is hepatically metabolized to bicarbonate. Research has shown that patients differ in their sensitivity to bicarbonate in the dialysate. For instance, in some patients excessive bicarbonate may result in alkalemia, whereas, in some patients insufficient bicarbonate may result in acidemia. Therefore, if citrate is used as the anti-coagulent, then it is important that the concentration of bicarbonate in the dialysate be relatively low, depending on the sensitivity of the individual patient. Usage of a low bicarbonate dialysate solution of the invention takes into account the bicarbonate derived from citrate, and as a result the total effective bicarbonate concentration is accounted for and effectively controlled. Thus, metabolic complications are effectively minimized. The low bicarbonate sterile solution of the invention typically contains a bicarbonate concentration within the range of 5-30 mmol/l, preferably between 20-30 mmol/l, and more preferably 25±2.5 mmol/l. The solutions with bicarbonate concentrations below 25 mmol/L may have sodium citrate added to them up to 20 mmol/L to act as an anticoagulant.

The benefit of such a low concentration of bicarbonate as 25 mmol/L is that if the patients bicarbonate level drops below this, bicarbonate diffuses from the dialysate across the semipermeable membrane to the patient correcting the problem. If there is an excess of bicarbonate in the blood (metabolic alkalosis) then bicarbonate will diffuse out into the dialysate effluent and be removed returning the patient toward normal.

In a first embodiment, the present invention provides a sterile calcium-free low bicarbonate concentrate comprising: sodium chloride (NaCl) 90.72±9.0 g/l, sodium bicarbonate (NaHCO3) 28.35±2.8 g/l, and magnesium chloride (MgCl2) 2.05±0.2 g/l.

The concentrate can be stored at room temperature, preferably for an extended period of time. In one embodiment, the concentrate can be stored for up to 48 months under suitable conditions. The concentrate may also contain potassium, dextrose and/or b-hydroxy-butyrate or other ketones including sodium citrate.

The invention further relates to a sterile solution comprising the low bicarbonate concentrate of the first embodiment and a physiologically acceptable diluent. The sterile solution comprises Na 140±14 mmol/l, Mg 0.75±0.07 mmol/l, Cl 116.5±11 mmol/l and HCO3 25.0±2.5 mmol/l. In a most preferred embodiment, sterile solution is typically used in conjunction with a citrate anti-coagulant protocol. It may also be used with systemic heparin anticoagulation or other anticoagulant systems for example low molecular weight heparin, prostacyclin, danaparoid, nafomestat mesylate etc.

The inventors have determined that the concentrates and sterile dilute solutions of the concentrates can be used in a number of novel applications including as a dialysate in hemodialysis of critically ill patients and as an infusate for hemofiltration.

The concentrates offer a convenient means to prepare sterile and pyrogen free solutions at the bedside or in the pharmacy to avoid extemporaneous mixing. The low bicarbonate concentrate of the first embodiment of the invention may be provided as a sterile concentrate in unit dosage to be added to a fixed volume of sterile water in PVC bags or as a prediluted sterile solution containing Na 140±14 mmol/l, Mg 0.75±0.07 mmol/l, Cl 116.5±11 mmol/l, and HCO3 25.0±2.5 mmol/l. The concentrate and the dilute solution contained in glass or CO2 impermeable plastic bags are stable and able to be stored for prolonged periods (up to 2 years). The storage must be at temperatures from 10° C. to 40° C.

DETAILED DESCRIPTION OF THE INVENTION

This invention generally relates to concentrates and corresponding diluted dialysis solutions with reduced bicarbonate concentrations. CRRT requires the addition of an anti-coagulent such as citrate to the dialysate to prevent thrombosis. Citrate is an organic acid which is hepatically metabolized to bicarbonate. Research has shown that patients differ in their sensitivity to bicarbonate in the dialysate. For instance, in some patients excessive bicarbonate may result in alkalemia, whereas, in some patients insufficient bicarbonate may result in acidemia. Therefore, if citrate is used as the anti-coagulent, then it is important that the concentration of bicarbonate in the dialysate be relatively low, depending on the sensitivity of the individual patient. Usage of a low bicarbonate dialysate solution takes into account the bicarbonate derived from citrate, and as a result the total effective bicarbonate concentration is accounted for and effectively controlled. Thus, metabolic complications are minimized.

The present inventors have developed a sterile calcium-free low bicarbonate concentrate containing magnesium, sodium, chloride and a low concentration of bicarbonate that can be used in a number of novel applications. In a first embodiment, the present invention provides a sterile calcium-free low bicarbonate concentrate comprising sodium chloride (NaCl) 90.72±9.0 g/l, magnesium chloride (MgCl2) 2.05±0.2 g/l, and sodium bicarbonate (NaHCO3) 28.35±2.8 g/l. The concentrate may also contain potassium, dextrose and/or ketones such as b hydroxy-butyrate. The concentrate can be stored at room temperature, preferably for an extended period of time. In one embodiment, the concentrate can be stored for at least up to 48 months.

In one aspect of the invention, the concentrates may be used in continuous renal replacement therapies (CRRT) such as dialysis and hemofiltration. The concentrates can be diluted in sterile physiologically acceptable diluents and used as a dialysis solution. The dialysis solutions of the invention provide a more physiologically acceptable dialysis solution when compared to lactate dialysis solutions containing glucose and lactate and/or calcium. The low bicarbonate concentrate of the present invention provides a dialysis solution that avoid the problems of prior art bicarbonate dialysis solutions in that it is highly stable i.e. calcium does not precipitate, and the concentrates can be stored for about up to 48 months. Typically, the low bicarbonate concentrates and diluted solutions can be used in conjunction with a regional citrate anti-coagulation protocol. Additionally, the low bicarbonate concentrate takes into account the bicarbonate which is derived from citrate, thus avoiding metabolic complications. Preferably, the dialysis solutions are used for acute hemodialysis in intensive care patients.

The low bicarbonate concentrates and dialysis solutions of the invention are cost effective because they facilitate process changes that increases efficiency by simplifying patient management, thus reducing nursing and medical staff time. They reduce or eliminate the need for corrective measures due to lactate or dextrose contained in other dialysates, lowering costs of extra syringes, needles, insulin, bicarbonate, etc. They also replace problematic lactate based peritoneal dialysis solutions used for dialysate in continuous hemodialysis all of which lead to a shorter number of days required in the intensive care unit (ICU).

It has been found that the low bicarbonate concentrates of the present invention and dialysis solutions prepared from the concentrates are very suitable for CRRT, and in particular in CRRT adapted for acute renal replacement therapy of critically ill patients in particular, patients in intensive care units. The stability and sterility of the dialysis concentrate of the invention necessarily results in reduced renal replacement therapy costs.

The low bicarbonate concentrates may be prepared by mixing the various components of the concentrates using conventional methods. The low bicarbonate concentrates of the invention may be prepared according to the constituent ranges, or according to the preferred amounts set forth herein to prepare a unit dose i.e. a dose amount that can be mixed with a predetermined amount of a sterile physiologically acceptable diluent (e.g. 1, 3 or 5 liters of sterile water) to prepare a dialysis solution.

The low bicarbonate concentrates may be used to produce dialysis solutions by mixing sterile physiologically acceptable diluents with the concentrates. Accordingly, in another aspect the invention provides dialysis solutions comprising the low bicarbonate concentrates of the invention and a physiologically acceptable diluent. Physiologically acceptable diluents which may be used in the dialysis solution of the invention include, but are not necessarily limited to sterile water and dextrose 5% in water (for injection).

The low bicarbonate solutions are generally prepared by mixing a unit dosage of concentrate, with 3 liters of a sterile physiologically acceptable diluent. Further to the first embodiment, the low bicarbonate dialysis solution may be prepared pre-diluted and stored in CO2 impermeable bags. It consists of the following in mmol per liter: Na 140±14 mmol/l, Mg 0.75±0.07 mmol/l, Cl 116.5±11 mmol/l, and HCO3 25.0±2.5 mmol/l. The dialysis solution may contain potassium, up to 4 mmol/liter, and/or b hydroxy-butyrate or other ketones, up to 5 mmol/liter. Preferably, the dialysis solution consists of the following in mmol per liter: Na 140, Mg 0.75, Cl 116.5, and HCO3 25.0.

If the dialysis solution is made in a PVC (polyvinyl chloride type) plastic container, it is advisable to use it within about 72 hours in order to avoid loss of bicarbonate through the plastic. The dialysis solution may be stored at a wide range of temperatures. For instance, it can either be stored at room temperature or be refrigerated. Calcium may be added to the diluent for CRRT, just prior to administration (M Leblanc et al, AJKD, 1995).

In a further aspect, the present invention provides a method for providing continuous renal replacement therapy to a patient comprising administering a sterile low bicarbonate dialysis solution comprising Na 140±14 mmol/l, Mg 0.75±0.07 mmol/l, Cl 116.5±11 mmol/l, and HCO3 25.0±2.5 mmol/l to a patient in need thereof. The present invention also provides a use of a concentrate according to the first embodiment comprising sodium chloride (NaCl) 90.72±9.0 g/l, magnesium chloride (MgCl2) 2.05±0.2 g/l, and sodium bicarbonate (NaHCO3) 28.35±2.8 g/l for preparing a dialysis solution for use in continuous renal replacement therapy.

The dialysis solution of the invention is preferably used to treat acute renal failure in critically ill patients. In contrast to prior art dialysis methods, the treatment typically does not involve incorporating calcium into the blood using the dialysis procedure. Therefore, the invention also contemplates a method for treating acute renal failure in a critically ill patient comprising dialyzing blood from the patient without introducing calcium into the blood removed from the patient during dialysis, and using a sterile dialysis solution prepared by mixing a sterile diluent with a sterile low bicarbonate concentrate according to the first embodiment comprising NaCl 90.72±9.0 g/l, MgCl2 2.05±0.2 g/l, and NaHCO3 28.35±2.8 g/l. The dialysis solution may additionally contain potassium, up to 4 mmol/liter, glucose up to 5 mmol/liter and/or b hydroxy-butyrate or other ketones, up to 5 mmol/liter.

The term "critically ill patient" or "critically ill patients" refers to patients that have a high mortality rate, acute renal failure, multiple organ failure, and multiple metabolic derangements. Critically ill patients which can be treated using the dialysis solution of the invention typically have acute renal failure and a high APACHE II score (Knaus W. A. Et al., Crit. Care Med. 13:818-827, 1985). An assessment of the number of failing organs may be performed using the procedure described in Jordan, D. A. Et al., Crit Care Med 15:897-904,1987. The bicarbonate concentrates and dialysis solutions of the invention are preferably administered to patients in intensive care who require dialysis and are hemodynamically unstable, or whose liver function is either impaired or at risk of impairment. Liver transplantation patients are especially difficult to manage and very often cannot handle any dialysate which contains lactate. Unable to transform the lactate in lactate buffered dialysis solutions to bicarbonate, they will go into acidosis if such solutions are used, and they require large doses of bicarbonate to correct pH imbalance.

The dialysis solutions of the invention are compatible with all systems used for CRRT including the commercially available systems such as the COBE Prisma Denver, Colo., Baxter CRRT System, Chicago, Ill., Hospital BSM22, Medolla, Italy, IMED Pump System, San Diego, Calif., Fresenius CRRT system, Dusseldorf, Germany or any other CRRT machine that uses peritoneal dialysate or other lactate-containing fluid or other bicarbonate based solutions as CRRT hemodialysate or infusate. When the dialysis solution is used with conventional systems for CRRT the consumption rate will typically be a unit dose of concentrate per hour assuming a dialysate flow of 1 liter per hour up to 2 liter per hour and a further 500 cc per hour of infusate.

The present invention includes kits for preparing dialysis solutions. In one embodiment, the present invention provides a kit for preparing a dialysis solution comprising (a) one 240 ml unit of a concentrate comprising sodium chloride (NaCl) 90.72±9.0 g/l, magnesium chloride (MgCl2) 2.05±0.2 g/l, and sodium bicarbonate (NaHCO3) 28.35±2.8 g/l and optionally (b) three liters of sterile water or another suitable diluent.

The concentrates and dialysis solutions of the invention may also be used for slow nocturnal hemodialysis. This is a form of dialysis where patients dialyse themselves at home overnight using a modified hemodialysis machine. In this embodiment, the concentrate would be added to clean water prepared for hemodialysis by water purification such as reverse osmosis or deionization as appropriate for local water supply. 80 ml of bicarbonate concentrate is added to each liter of clean water to make 1080 ml dialysate. In this embodiment, calcium must be added to the dialysate of the invention prior to administration to the patient. This may be accomplished by adding calcium to each liter of the dialysis solution. Calcium may be added to produce a final calcium concentration according to local protocol. To produce a final calcium concentration in the range 1.25-1.75 mmol/L (5.0-7.0 mg/dL) calcium chloride 10% solution (100 mg/ml, 1.4 mEq/ml) 1.8-2.5 ml is added per 1080 ml of dialysate. Alternatively calcium gluconate 10% solution (100 mg/dl, 0.465 mEq/ml) 5.4-7.6 ml may be added per 1080 ml of dialysate to produce the same final calcium concentrations 1.25-1.75 mmol/L (5.0-7.0 mg/dl). Calcium may be added aseptically using a syringe and needle or through the use of a split bag system containing the calcium in a separate container which is then added to the solution prior to patient administration.

The dialysis solution of the invention, either the concentrate or the diluted solution, may be contained in a plastic container (bag) for use at the bedside.

In one aspect of the invention, the solution will be prepared to a desired concentration for dialysis; Na 140±14 mmol/l, Mg 0.75±0.07 mmol/l, Cl 116.5±11 mmol/l, and HCO3 25.0±2.5 mmol/l. The sterile water and all electrolytes, except calcium, are mixed, and if desired, diluted, and placed in a bag impermeable to carbon dioxide. At the time of dialysis, calcium may be added from, for example, a pre-filled syringe. Calcium may be added to produce a final calcium concentration according to local protocol. To produce a final calcium concentration in the range 1.25-1.75 mmol/L (5.0-7.0 mg/dl) calcium chloride 10% solution (100 mg/ml, 1.4 mEq/ml) 1.8-2.5 ml is added per 1080 ml of dialysate. Alternatively calcium gluconate 10% solution (100 mg/dl, 0.465 mEq/ml) 5.4-7.6 ml may be added per 1080 ml of dialysate to produce the same final calcium concentrations 1.25-1.75 mmol/L (5.0-7.0 mg/dL).

In one embodiment of the invention, the pre-filled syringe with calcium is sold in a kit form with the bag. In another, a section of the bag will be sealed off and filled with a calcium solution. When required, the separating mechanism membranes within the bags will be broken, and calcium will be released into the portion bag containing the sterile water and the other electrolytes. In one embodiment the calcium will be injected by pre-attached syringe to the spike attachment port of the bag. After injection the syringe is broken away revealing the spike site. This allows for aseptic spiking and a failsafe device to prevent spiking of the bag without first injecting calcium. This would be the preferred embodiment for use in peritoneal dialysis where calcium inclusion is essential.

Containers, such as bags, which are impermeable to carbon dioxide are selected for use in the present invention. For example, a bag may be made with three layers of plastic material, sandwiched together (see for example, bag produced by Bieffe Medital, 20157 Milano, 41100 Modena, Italy, Stedim San Diego, Advanced Scientifics Pa.)

In a further aspect of the invention, the concentrates may be used as an infusate in hemodialysis. Consequently, the present invention provides a use of a sterile calcium-free concentrate according to the first embodiment for preparing an infusate for hemofiltration, wherein said concentrate comprises sodium chloride (NaCl) 90.72±9.0 g/l, magnesium chloride (MgCl2) 2.05±0.2 g/l, and sodium bicarbonate (NaHCO3) 28.35±2.8 g/l. The present invention also provides a method for hemofiltration comprising administering a sterile dialysis solution comprising Na 140±14 mmol/l, Mg 0.75±0.07 mmol/l, Cl 116.5±11 mmol/l, and HCO3 25.0±2.5 mmol/l to a patient in need thereof. The infusate may be prepared by mixing 3000 ml of sterile water to 240 ml of the concentrate.

The infusate can be prepared when needed or can be prepared and stored in a suitable container, such as a bag, which is impermeable to carbon dioxide, until it is needed.

The amounts and components of the concentrates and dialysis solutions of the invention may be modified to adapt to their use in cardiovascular surgery, peritoneal dialysis, hemodiafiltration, hemofiltration, and as an electrolyte solution.

I claim:

1. A sterile calcium free low bicarbonate dialysis concentrate composition containing sodium chloride, magnesium chloride and sodium bicarbonate for continuous renal replacement therapy and for use in the preparation of a sterile calcium free dialysis solution comprising sodium chloride (NaCl), magnesium chloride ($MgCl_2$), and a concentration of sodium bicarbonate ($NaHCO_3$) sufficiently low so as to allow preparation of the sterile calcium free dialysis solution for continuous renal replacement therapy, having ion concentrations of Na 140±14 mmol/l, Mg 0.75±0.07 mmol/l, Cl 116.5±11 mmol/l, and $HCO_3$ 25.0±2.5 mmol/l.

2. A sterile calcium free low bicarbonate dialysis concentrate composition containing sodium chloride, magnesium chloride and sodium bicarbonate for continuous renal replacement therapy and for use in the preparation of a sterile calcium free dialysis solution comprising sodium chloride (NaCl), magnesium chloride ($MgCl_2$), and a concentration of sodium bicarbonate ($NaHCO_3$) sufficiently low so as to allow preparation of the sterile calcium free dialysis solution for continuous renal replacement therapy, having ion concentrations of Na 140±14 mmol/l, Mg 0.75±0.07 mmol/l, 01116.5±11 mmol/l, and $HCO_3$ of from 20 to less than 30 mmol/l.

3. A kit for preparing a sterile calcium free dialysis solution comprising the sterile calcium free dialysis concentrate composition of claim 1 or 2 and optionally instructions for use.

4. The kit of claim 3, further comprising sterile water sufficient to dilute the concentrate to a sterile calcium free dialysis solution comprising Na 140±14 mmol/l, Mg 0.75±0.07 mmol/l, Cl 116.5±11 mmol/l, and $HCO_3$ 25.0±2.5 mmol/l.

5. A method of preparing a sterile calcium free dialysis solution comprising diluting a sterile calcium free dialysis concentrate composition of claim 1 or 2 in a sufficient amount of sterile water to prepare a sterile calcium free dialysis solution comprising Na .140±14 mmol/l, Mg 0.75±0.07 mmol/l, Cl 116.5±11 mmol/l, and $HCO_3$ 25.0±2.5 mmol/l.

6. A method for providing continuous renal replacement therapy to a patient comprising administering a sterile calcium free dialysis solution prepared according to the method of claim 5 in conjunction with a regional citrate anti-coagulant solution to a patient in need thereof.

7. A method of preparing a sterile calcium free dialysis solution or infusate comprising diluting a sterile calcium free dialysis concentrate composition of claim 1 or 2 in a sufficient amount of sterile water to prepare a sterile calcium free dialysis solution or infusate comprising Na 140±14 mmol/l, Mg 0.75±0.07 mmol/l, Cl 116.5±11 mmol/l, and $HCO_3$ 25.0±2.5 mmol/l.

8. A method for treating acute renal failure in a critically ill patient without introducing calcium into the blood removed from the patient during dialysis comprising administering a sterile calcium free dialysis solution prepared according to the method of claim 7 in conjunction with a regional citrate anti-coagulant solution to a patient in need thereof.

9. A method for providing hemofiltration to a patient comprising administering a sterile calcium free infusate prepared according to the method of claim 7 in conjunction with a regional citrate anti-coagulant solution to a patient in need thereof.

* * * * *